United States Patent [19]

Bowman

[11] Patent Number: 4,891,349
[45] Date of Patent: Jan. 2, 1990

[54] CATALYST FOR PREPARING AMINES

[75] Inventor: Robert G. Bowman, Midland, Mich.

[73] Assignee: The Dow Chemical Company, Midland, Mich.

[21] Appl. No.: 268,908

[22] Filed: Nov. 7, 1988

Related U.S. Application Data

[62] Division of Ser. No. 732,978, May 13, 1985, Pat. No. 4,806,690.

[51] Int. Cl.$^4$ .................. B01J 21/06; B01J 23/72; B01J 23/80
[52] U.S. Cl. .................... 502/329; 502/331
[58] Field of Search ............... 502/329, 331

[56] References Cited

U.S. PATENT DOCUMENTS

| | | | |
|---|---|---|---|
| 3,347,926 | 10/1967 | Zech | 564/480 |
| 3,520,933 | 7/1970 | Adam et al. | 564/480 |
| 3,654,370 | 4/1972 | Yeakey | 564/480 |
| 4,014,933 | 3/1977 | Boettger et al. | 564/480 |
| 4,152,353 | 5/1979 | Habermann | 564/480 |
| 4,153,581 | 5/1979 | Habermann | 564/480 |
| 4,409,399 | 10/1983 | Swift et al. | 564/473 |

OTHER PUBLICATIONS

IUPAC, Manual of Symbols and Terminology for Physicochemical Quantities and Units: Part II: Heterogeneous Catalysis, pp. 371–372.
Bartok, M. et al., J. of Catalysis, vol. 100, pp. 39–44, (1986).
Advances in Catalysis, vol. 26, pp. 43–46.

Primary Examiner—W. J. Shine

[57] ABSTRACT

A method for producing amines, the method comprising contacting at reactive conditions at least one alcohol, aldehyde or ketone, or a mixture thereof, with an aminating agent in the presence of a catalyst, is improved by employing as the catalyst a composition comprising cobalt, copper, and a third component selected from a group consisting of iron, zinc, zirconium and mixtures thereof.

10 Claims, No Drawings

CATALYST FOR PREPARING AMINES

This is a divisional, of application Ser. No. 732,978, filed May 13, 1985, now U.S. Pat. No. 4,806,690.

BACKGROUND OF THE INVENTION

The present invention relates to an improved method of producing amines from alcohols, aldehydes, ketones, and mixtures thereof. In one aspect, the invention relates to an ammonolytic method while in another aspect it relates to a catalyst useful therein.

The amination of alcohols, aldehydes, and ketones using catalysts containing nickel, copper or both is known. For example, see U.S. Pat. Nos. 4,153,581; 4,409,399; 4,152,353 and the patents cited therein. Habermann, in U.S. Pat. No. 4,153,581, discloses a method of preparing amines using a catalyst comprising from about 20 to about 90 percent cobalt, from about 8 to about 72 percent copper, and from about 1 to about 16 percent of a third component selected from the group consisting of iron, zinc, zirconium and mixtures thereof. The catalyst of U.S. Pat. No. 4,153,581 must be at least 20 percent cobalt, a relatively expensive metal. It would be desirable, for practical reasons, to provide a catalyst for the amination of alcohols, etc., which would have equal or superior activity at lower cost.

SUMMARY OF THE INVENTION

According to the present invention, a method of producing amines, the method comprising contacting at reactive conditions at least one alcohol, ketone, or aldehyde with an aminating agent in the presence of an ammonolytic catalyst, is surprisingly improved by using as the catalyst a composition comprising (calculated in mole percent and on an oxide-free basis) from about 1 to less than about 20 percent cobalt, about 75 to about 95 percent copper, and about 1 to about 16 percent of a third component selected from the group consisting of iron, zinc, zirconium and mixtures thereof. These compositions demonstrate comparable or superior ammonolytic activity at lower catalyst costs.

DETAILED DESCRIPTION OF THE INVENTION

The catalytic compositions of the present invention are generally 3-component compositions comprising (calculated in mole percent and on an oxide-free basis): (1) from about 1 to less than about 20 percent cobalt; (2) from about 75 to about 95 percent copper; and (3) from about 1 to about 16 percent of a third component selected from the group consisting of iron, zinc, zirconium and mixtures thereof.

Compositions wherein the third component comprises only iron, or only zinc or only zirconium are preferred over compositions wherein the third component comprises a mixture of these components. Compositions wherein the third component comprises only zirconium are particularly preferred. The preferred amount of zirconium is from about 5 to about 6 percent. Preferably, the composition includes from about 6 to about 17 percent cobalt. The preferred amount of copper is from about 79 to about 89 percent.

These compositions can be used either unsupported or supported. Typical supports include: alumina, silica, zirconia, zircon (a mixture of zirconia and silica), magnesia, and various cation-exchange resins, such Dowex® HCR, Dowex® MSC-1, and Dowex® CCR-2 (all available from The Dow Chemical Company and comprising a sulfonated styrene-divinylbenzene copolymer matrix). If the composition is supported, the metal loading (on an oxide-free basis) is usually at least about 0.5 percent and preferably at least about 10 percent of the total weight (support plus composition). The maximum metal content can vary to convenience.

The catalytic compositions of this invention are readily prepared by any number of different methods but are typically prepared by first precipitating the metal components from their salts, e.g., nitrates, chlorides, sulfates, acetates, etc., in a basic, aqueous solution, e.g., sodium or ammonium carbonate, sodium or potassium hydroxide, alkali(ne earth) metal oxalates, silicates or aluminates, etc. The metal precipitate is then washed, filtered and dried at an elevated temperature, e.g., 60° C.–180° C., and the dry precipitate is then decomposed at a temperature between about 200° C. and about 400° C. for a suitable period of time, e.g., 2 hours, to the corresponding oxides. If desired, preparation of the composition can commence with commercially available oxides rather than first preparing the oxides as here described. The resulting oxide mixture is then reduced with hydrogen, sodium borohydride, hydrazine, a reducing metal of greater oxidation potential than cobalt, carbon monoxide or some other suitable reducing agent, such as the reaction mixture, i.e., the catalyst can be reduced in the reactor using the reactants. The degree of reduction is temperature dependent but generally the first two components (cobalt and copper) are reduced to the active metal while the third component, i.e., zinc, iron, zirconium or a mixture thereof, remains an oxide. When this reduction is with hydrogen, a temperature between about 150° C. and about 250° C. for about 6 to 7 hours is usually adequate. The reduced catalyst is thereafter generally handled in the absence of air. If a supported catalyst is desired, the metal salts can be precipitated directly upon or with the carrier (support).

These compositions can also be prepared from suitable alloys of the three components and at least one leachable fourth component. For example, an alloy of cobalt, copper, zirconium and aluminum can be formed and subjected to caustic whereby the aluminum is leached from the alloy. The resulting Raney-like structure is then ready for use.

A catalytic amount of the composition is required for the practice of this invention. The minimum amount of catalyst required will vary with the method reagents and conditions, but a typical minimum amount of about 0.1 weight percent, and preferably about 1 weight percent, based on the weight of the starting materials, is employed. Practical considerations, such as convenience, catalyst recovery, economy, etc., are the only limitations upon the maximum amount of catalyst that can be used.

Any alcohol that can be used in known ammonolytic methods can be used in the practice of this invention. These alcohols comprise a wide variety of hydroxy-containing materials. Representative alcohols include: primary and secondary alcohols, such as alkanols of 1 to about 18 carbon atoms, e.g., methanol, n-propanol, isopropanol, n-butanol, sec-butanol, isobutanol, pentanol, hexanol, 2-ethylhexanol, tridecanol, stearyl alcohol, etc.; cycloalkanols of 5 to 12 carbon atoms, e.g., cyclohexanol, cycloheptanol, etc.; aralkanols of 7 to about 40 carbon atoms, e.g., benzyl alcohol, 2-phenyl ethanol, etc.; polyhydric alcohols of 2 to about 15 carbon atoms, e.g., ethylene glycol, propylene glycol, 1,3-butanediol, 1,4-butanediol, 1,5-pentanediol hexamethylene glycol, decamethylene glycol, 1,12-dihydroxyoctadecane, glycerol, etc.; polymeric polyhydric alcohols, e.g., polyvinyl alcohol; glycol ethers and polyalkylene glycol ethers, e.g., methyl glycol, ethyl glycol, butyl glycol, diethylene glycol, triethylene glycol, tetraethylene glycol, higher polyethylene glycols, dipropylene glycol, tripropylene glycol, polypropylene glycol ether, polybutylene glycol ether, etc.; aminated alcohols, such as alkanolamines, e.g., ethanolamine, propanolamine, isopropanolamine, hexanolamine, diethanolamine, diisopropanolamine, dimethylethanolamine, etc.; and aminated polyhydric alcohols and glycol ethers, e.g., aminated polyethylene glycol, etc. Other suitable hydroxy-containing compounds are disclosed in U.S. Pat. Nos. 3,347,926, 3,654,370 and 4,014,933.

Any aldehyde or ketone that can be produced from the dehydrogenation of the alcohols here used can also be used in the practice of this invention. Representative aldehydes include: methanal, ethanal, propanal, butanal, cyclohexanal, benzylaldehyde, and aldehydes prepared from the dehydrogenation of polyhydric alcohols, polymeric polyhydric alcohols, glycol ethers and polyalkylene glycol ethers, aminated alcohols, aminated polyhydric alcohols and glycol ethers, etc. Representative ketones include: propanone, butanone, 2-pentanone, 3-pentanone, 3-methyl-2-butanone, 1-phenyl-2-propanone, acetophenone, n-butyrophenone, benzophenone, 3-nitro-4'-methylbenzophenone and ketones prepared from the dehydrogenation of polyhydric alcohols, polymeric polyhydric alcohols, glycol ethers and polyalkylene glycol ethers, aminated alcohols, aminated polyhydric alcohols and glycol ethers, etc.

As used herein, "at least one alcohol, aldehyde or ketone, or a mixture thereof," means that these compounds can be used either singly (which is preferred), i.e., only one alcohol, only one aldehyde or only one ketone, or in a mixture comprising a combination of these compounds, e.g., a mixture of two or more alcohols, or two or more aldehydes, or two or more ketones, or of at least one alcohol and at least one aldehyde, or of at least one aldehyde and at least one ketone, or of at least one alcohol and at least one ketone, or of at least one alcohol, at least one aldehyde and at least one ketone.

The term "alcohol" includes those compounds containing both a hydroxy function and a carbonyl function and the term "aldehyde" includes those compounds without a hydroxy function but containing both an aldehyde carbonyl and a ketone carbonyl. Aldehydes are preferred to ketones and alcohols are preferred to aldehydes.

The aminating agents of this invention are ammonia or primary or secondary amines. The primary and secondary amines generally have alkyl radicals of 1 to about 12 carbon atoms or cycloalkyl radicals of 5 to 8 carbon atoms or aralkyl radicals of 7 to about 40 carbon atoms and include such compounds as: methylamine, dimethylamine, ethylamine, diethylamine, n-butylamine, sec-butylamine, isobutylamine, ethylenediamine, benzylamine, aniline, etc. Other suitable amines include cyclic amines which can contain hetero atoms other than nitrogen, such as oxygen, and these compounds include: morpholine, pyrrolidine, piperidine, piperazine, etc. When ammonia is the aminating agent, primary amines are obtained; when a primary amine is the aminating agent, secondary amines are obtained; when a secondary amine is the aminating agent, tertiary amines are obtained. These aminating agents, like the alcohols, aldehydes and ketones, can also be used either singly or in combination with one another. The former is preferred.

Stoichiometric amounts of alcohol and aminating agent are required for the practice of this invention. However, for reasons of convenience and efficiency it is preferable to practice this invention with a stoichiometric excess of aminating agent to alcohol. Typically, a minimum aminating agent:alcohol mole ratio of about 1:1 and preferably of about 5:1 is employed. Practical considerations, such as economy, reaction equipment, etc., are the only limitations upon the maximum said ratio but these considerations prefer a mole ratio of about 200:1 and more preferably of about 100:1. The typical aminating agent:aldehyde, ketone or mixture mole ratios are generally the same as the here recited aminating agent:alcohol mole ratios.

The method of this invention generally employs hydrogen. The amount of hydrogen employed, if employed, can vary to convenience but a typical minimum hydrogen:alcohol mole ratio is at least about 0.1:1 and preferably is at least about 1:1. A typical maximum mole ratio is about 50:1 and preferably is about 20:1. Again, the typical hydrogen:aldehyde, ketone or mixture mole ratios are generally the same as the here recited hydrogen:alcohol mole ratios.

Although conventional method conditions can here be used, the superior catalytic activity of this invention's composition permits the ammonolytic process to proceed at lower temperatures and pressures. For example, this invention can be practiced at a temperature of at least about 75° C. although preferred reaction rates are obtained at a temperature of at least about 120° C. Pressures are of course dependent upon temperature but a minimum pressure of about 50 psi (345 kPa) can be used. A minimum pressure of about 500 psi (3450 pKa) is preferred, and a minimum pressure of about 1,000 psi (6900 kPa) is most preferred. Again, practical considerations are the only limitations upon the maximum temperature and pressure but a maximum temperature of about 400° C. and a maximum pressure of about 10,000 psi (69,000 kPa) are preferred. A more preferred maximum temperature is about 250° C. and a more preferred maximum pressure is about 3,000 psi (20,700 kPa).

The invention can be practiced on either a continuous or batch operation, in both the liquid and gas phases, and either neat or in the presence of an inert solvent. By "inert" is meant that the solvent is essentially nonreactive with the method reagents and products at the method conditions. Exemplary solvents include aliphatic and aromatic hydrocarbons, such as hexane, heptane, cyclohexane, benzene, toluene, xylene, etc.; and nonreactive tertiary amines, such as pyridine, picoline, lutadine, etc. Moreover, this method can be practiced in either the presence or absence of water, although if water is present it is preferred that it is not present in amounts greater than about 50 weight percent of the alcohol, aldehyde, ketone or mixture.

Whether the amines produced by this invention are primary, secondary, or tertiary depends not only upon the aminating agent employed, as earlier noted, but also upon the particular method conditions employed. Short contact time, e.g., between about 0.1 seconds and about 15 minutes, excess ammonia and low temperature and pressure generally favor the production of primary amines. As the aminating agent:alcohol, aldehyde, ketone or mixture mole ratio decreases and/or the temperature increases and/or the contact time increases, secondary and tertiary amines form a larger percentage of the method product. However, longer reaction time favors greater amination of the alcohol. Accordingly, by appropriate selection of aminating agent and method conditions, it is possible to influence the method product mix of primary, secondary and tertiary amines.

The following examples are illustrative of certain specific embodiments of this invention. Unless otherwise noted, all parts and percentages are by weight.

SPECIFIC EMBODIMENTS

General Procedure for Catalyst Preparation

A first solution is prepared from 2 liters of water and varying amounts of zirconium and copper compounds of the catalytic metals. A small amount of green solid remains undissolved. For Catalyst 1 a few drops of concentrated $HNO_3$ is added to dissolve the green solid, and for Catalysts 2–6, the green solid is removed by filtration and discarded. For Catalysts 2-6 a cobalt compound is added to the solution after the green solid is discarded. Then, sufficient water is added to increase the volume of the solution to 3.5 liters.

A second solution is prepared from 2 liters of water and a varying amount of $(NH_4)_2CO_3$. Then, sufficient water is added to the solution to increase its volume to 3.5 liters.

A third solution is prepared as follows. The first and second solutions are added with stirring over a period of about 20 minutes to a flask containing 1 liter of water. A precipitate starts to form in the flask, and the third solution (slurry) is maintained at a pH of approximately 6.5-7.0 during the precipitation by controlling the rate at which the first and second solutions are added to the flask. The precipitate and the mother liquor are stirred for 1 additional hour; not all of the color is removed from the solution during the precipitation.

The precipitate is filtered and washed with 3 liters of water and is again filtered. The precipitate is resuspended in 3 liters of water and is stirred rapidly for 0.5 hours and is then filtered. The filter cake is then dried at 110° C.–120° C. for about 20 hours. The dried material is crushed (>40 mesh) and heated at 300° C. for 1.5 hours in air; then the material is recrushed (>40 mesh). The crushed material is placed in a rubber bag and compressed at 7500 psi (51,700 kPa) using a hydrostatic press. The compressed material is crushed giving 8–16 mesh particles.

The crushed material is reduced in 18 percent $H_2$ in $N_2$ at 175° C. for 4 hours prior to use as a catalyst for reductive amination of monoethanolamine (hereinafter MEA). The catalyst is not exposed to any $O_2$ after reduction with $H_2$.

Comparative Catalyst 1 is a copper-zirconium catalyst which is free of cobalt, and contains 0 cobalt-95 copper-5 zirconium (shorthand form for 0 mole percent Co, 95 mole percent Cu, and 5 mole percent Zr on an oxide-free basis).

Comparative Catalysts 2–4 are prepared using the teaching of U.S. Pat. No. 4,153,581.

Preparations 5 and 6 illustrate preparation of catalysts of the present invention These catalysts contain low amounts of Co and high amounts of Cu.

TABLE I

| | Catalyst Preparation Details - Compounds and Amounts used in Solutions | | | |
|---|---|---|---|---|
| Catalyst No. | First Solution | | | Second Solution |
| | $ZrO(NO_3)_2.2H_2O$ | $Cu(NO_3)_2.2.5H_2O$ | $CO(NO_3)_2.6H_2O$ | $(NH_4)_2CO_3$ |
| C.E. 1 | 20.63 g (0.0772 mole) | 340.38 g (1.463 mole) | — | 290.38 g |
| C.E. 2 | 21.93 g | 38.13 g | 405.74 g (1.3941 mole) | 264.40 g |
| C.E. 3 | 21.79 g | 75.87 g | 355.41 g | 266.79 g |
| C.E. 4 | 21.55 g | 176.38 g | 220.43 g | 300.87 g |
| Ex. 5 | 21.14 g | 225.34 g | 114.20 g | 300.13 g |
| Ex. 6 | 20.83 g | 306.87 g | 45.17 g | 300.12 g |

TABLE II

| | Analysis of Catalyst Compositions | | | | | | |
|---|---|---|---|---|---|---|---|
| Catalyst No. | Analysis (mole %) | | | Bulk Density (g/cc) before reduction | Surface Area ($m^2/g$) | | Total $H_2$ Adsorption(cc/g) after reduction |
| | Co | Cu | Zr | | before reduction | after reduction | |
| C.E. 1 | 0 | 95.3 | 4.7 | 1.140 | 64.9 | 22.2 | 0.537 |
| C.E. 2 | 74.9 | 16.1 | 9.07 | 0.801 | 118.7 | 88.3 | 7.179 |
| C.E. 3 | 63.0 | 29.8 | 7.22 | 0.752 | 133.6 | 71.6 | 5.306 |
| C.E. 4 | 37.2 | 55.9 | 6.84 | 0.909 | 106.5 | 56.7 | 3.408 |
| Ex. 5 | 15.0 | 79.0 | 6.00 | 0.992 | 87.4 | 30.0 | 1.055 |
| Ex. 6 | 5.85 | 88.7 | 5.50 | 1.50 | 65.0 | 20.1 | 0.532 |

General Procedure for the Reductive Amination of MEA

Catalysts 1–6 are each employed for the reductive amination of MEA. The reductive amination of MEA is run in a continuous flow system. The temperature of the reaction is 170° C. and the pressure is 1500 psi (10,300 kPa) with a residence time of 10 minutes. The feed is a mixture of MEA, $NH_3$, and $H_2$. The amounts employed are 1200 g (20 moles) of MEA, 2900 g (170 moles) of $NH_3$, and 750 psi (5200 kPa) $H_2$. Mole ratio: $NH_3/MEA=8.5$; weight ratio: $NH_3/MEA=2.4$. The amount of catalyst used is 25 cc (before reduction of the catalyst).

The products are collected in a product tank; the venting $NH_3$ is passed through the sample collection bottle at −23° C. prior to venting. Each hour the product collection tank is emptied into the sample collection bottle at −23° C. and a new sample collection bottle is then added to the system. The collected samples are warmed o room temperature and then are analyzed via gas chromatography.

The results are summarized in Tables III and IV.

TABLE III

| Catalyst No. | Selectivity for Reduction Amination of MEA at 170° C. and 1500 psi (10,300 kPa) | | | | | | | |
|---|---|---|---|---|---|---|---|---|
| | EDA % | DETA % | TETA % | Total EDA DETA TETA | PIP % | AEP % | Total Cyclics | AEEA % |
| C.E. 1 | 61 | 0 | 0 | 61 | 20 | 0 | 20 | 18 |
| C.E. 2 | 52 | 8 | 4 | 64 | 18 | 3 | 21 | 14 |
| C.E. 3 | 55 | 12 | 3 | 70 | 12 | 4 | 16 | 13 |
| C.E. 4 | 37 | 14 | 10 | 61 | 15 | 3 | 18 | 20 |
| Ex. 5 | 47 | 17 | 13 | 77 | 12 | 2 | 14 | 11 |
| Ex. 6 | 45 | 16 | 9 | 70 | 11 | 2 | 13 | 18 |

MEA - monoethanolamine
EDA - ethylenediamine
DETA - diethylenetriamine
TETA - triethylenetetramine
PIP - Piperazine
AEP - aminoethylpiperazine
AEEA - aminoethylethanolamine Table III illustrates that the catalysts of the present invention (5 and 6) advantageously produce fewer cyclic compounds, i.e., PIP and AEP. The cyclic compounds are undesirable in that they lead to increased product color. Unexpectedly, catalysts 5 and 6 produce relatively more of the desired di- and triamines (DETA and TETA).

TABLE IV

| Catalyst No. | Activity for the reductive amination of MEA at 170° C. and 1500 psi (10,300 kPa) | | | |
|---|---|---|---|---|
| | % Conversion For 25 cc of Catalyst | % Conversion Per Gram of Catalyst | Turnover Per Surface Active Site Per Second, $N_t$ ($\times$ 1000) [based on $H_2$ Absorption] | % Conversion Per $m^2$ ($\times$ 1000) |
| C.E. 1 | 3 | 0.1 | 4 | 5 |
| C.E. 2 | 57 | 2.8 | 8 | 32 |
| C.E. 3 | 59 | 3.1 | 12 | 44 |
| C.E. 4 | 61 | 2.8 | 16 | 47 |
| Ex. 5 | 70 | 2.8 | 50 | 94 |
| Ex. 6 | 40 | 1.4 | 50 | 70 |

In Table IV it can be seen that the catalysts of the present invention give conversions/$m^2$ which are at least about 70 percent. Surprisingly, on a per surface-active site basis, the catalysts of the present invention are at least about 3 times more active for the reductive amination of MEA than are the catalysts in U.S. Pat. No. 4,153,581. Thus, the catalysts of the present invention are more productive than the catalysts of U.S. Pat. No. 4,153,581.

WHAT IS CLAIMED IS:

1. A catalyst for preparing amines from at least one alcohol, aldehyde or ketone, or a mixture thereof, the catalyst comprising, calculated on an oxide-free basis:

(1) from about 1 to less than about 20 percent cobalt;
(2) from about 75 to about 95 percent copper; and
(3) from about 1 to about 16 percent of a third component selected from the group consisting of iron, zinc, zirconium and mixtures thereof.

2. The catalyst of claim 1 comprising from about 5 to about 6 percent zirconium.

3. The catalyst of claim 1 wherein the third component is only iron, only zinc, or only zirconium.

4. The catalyst of claim 1 wherein the third component is only iron.

5. The catalyst of claim 1 wherein the third component is only zinc.

6. The catalyst of claim 1 wherein the third component is only zirconium.

7. The catalyst of claim 6 having from about 5 to about 6 percent zirconium.

8. The catalyst of claim 1 comprising from about 6 to about 17 percent cobalt.

9. The catalyst of claim 8 wherein the third component is only zirconium.

10. The catalyst of claim 9 comprising from about 5 to about 6 percent zirconium.

* * * * *